United States Patent [19]

Sagen et al.

[11] Patent Number: 4,753,635
[45] Date of Patent: Jun. 28, 1988

[54] INDUCING ANALGESIA BY IMPLANTATION OF CELLS RELEASING NEUROACTIVE SUBSTANCES

[76] Inventors: Jacqueline Sagen, 6724 N. Rockwell St., Chicago, Ill. 60645; Mark Perlow, 1253 Fitzgerald Dr., Munster, Ind. 46321; George D. Pappas, 506 W. Roscoe St., Chicago, Ill. 60657; Harvey B. Pollard, 11008 Lamplighter Ln., Potomac, Md. 20854

[21] Appl. No.: 866,479

[22] Filed: May 23, 1986

[51] Int. Cl.$^4$ .............................................. A61F 2/66
[52] U.S. Cl. .................................... 604/49; 514/818; 604/891.1
[58] Field of Search ................ 128/1 R; 604/890–891, 604/31, 48–50; 514/809, 816–818, 21; 435/244–245

[56] References Cited

U.S. PATENT DOCUMENTS

| | | | |
|---|---|---|---|
| 4,264,492 | 4/1981 | Stein | 514/809 |
| 4,353,888 | 10/1982 | Setton | 623/11 |
| 4,371,463 | 2/1983 | Pert et al. | 514/809 |
| 4,388,236 | 6/1983 | Stein | 435/172.3 |

OTHER PUBLICATIONS

Freed et al., Transplanted Adrenal Chromaffin Cells in Rat Brain Induce Lesion Induced Rotational Behavior, Nature 292: 351–352 (1981).
Backlund et al. Transplantation of Adrenal Medullary T. Tissup to Striatum in Parkinsonism, Neural Grafting in the Mammalion Central Nervous System, pp. 551–556 (1985).
Snyder, Solomon H., *Opiate Receptors and Internal Opiates,* Scientific American, Mar. 1977, pp. 44–56.
Mizobe, Fumio and Livett, Bruce G., *Nicotine Stimulates Secretion of Both Catecholamines and Acetylcholinesterase from Cultured Adrenal Chromaffin Cells,* Journal of Neuroscience, vol. 3, No. 4, pp. 871–876, Apr. 1983.
Olson et al., *Transplantation in Parkinsons Disease,* Arnals of the New York Academy of Sciences, vol. 457, pp. 105–126, 1985.
J. Neurochem 36(3) 1981 886–892, Advances in Biochemical Psychopharmocology, vol. 22, pp. 571–580.

*Primary Examiner*—C. Fred Rosenbaum
*Assistant Examiner*—Sharon Rose
*Attorney, Agent, or Firm*—Holman & Stern

[57] ABSTRACT

A method of inducing analgesia or reducing pain is described. The method involves implanting in the central nervous system of a host susceptible to pain, living material capable of releasing effective amount of analgesic substance when interacted with a stimulus which induces said material to release analgesic amount of said substance. The procedure described herein reduces sensitivity to intractable pain.

14 Claims, 7 Drawing Sheets

INDUCING ANALGESIA BY IMPLANTATION OF CELLS RELEASING NEUROACTIVE SUBSTANCES

BACKGROUND OF THE INVENTION

1. Technical Field

The present invention is related to producing analgesia or reducing pain by implantation of cellular material in the central nervous system (CNS) of a host susceptible to pain sensation. More particularly, the present invention is related to the implantation of isolated chromaffin cells or adrenal medullary tissue in the brain stem or spinal cord for producing analgesia when the implanted tissue or cell is induced to release nociceptor interacting substances.

2. State of the Art

Reports of successful implantation of nonhomologous neural tissue to the central nervous system without immunological rejection have been known and these reports Holman & Stern, Chartered Folio P49667 have created interest in the potential of such transplants for restoring functional deficits. Improvements in reproductive behavior, cognition and motor behavior in lesioned animals have been reported following the implantation of appropriate fetal neuronal tissue. Implants of adrenal chromaffin cells have been shown to survive for long periods of time when transplanted into the central nervous system (Perlow et al., 1980, Proc. Natl. Acad. Sci. 77:5278-5281). Recently, adrenal medullary homografts have been implanted in the striatum of human Parkinson patients with encouraging results (Backlund et al., 1985, J. Neurosurg. 62:169-173). However, modulation of pain sensitivity by implants of living cells or tissue in the CNS has not heretofore been attempted. Since pain is not necessarily the result of damaged neuronal tissue, it is essential that the function of neural implants in intact, non-lesioned systems be assessed when determining pain sensitivity.

SUMMARY OF INVENTION

It is, therefore, an object of the present invention to establish the efficacy for pain relief of CNS implants of such cells or tissue which release neuroactive substances when induced with suitable stimulus.

It is a further object of the present invention to provide a method of producing analgesia or reducing pain by implanting in the central nervous system such cells or tissues which release nociceptor reacting substances when induced with a suitable stimulus.

Other objects and advantages will become evident as the detailed description of the invention proceeds.

BRIEF DESCRIPTION OF DRAWINGS

These and other objects, features and many of the attendant advantages of the invention will be better understood upon a reading of the following detailed description when considered in connection with the accompanying drawings wherein:

FIG. 2 shows the effect of spinal cord adrenal medullary transplants on pain sensitivity. The ordinate is the threshold for response to noxious stimuli as assessed by the tail flick test (A), hot plate test (B) or paw pinch test (C). Each point represents the mean ±S.E.M. The abscissa is the time course of response to noxious stimuli following nicotine stimulation (s.c.). Time 0 indicates the pre-injection values. The arrowhead indicates the point at which nicotine (0.1 mg/kg, s.c.) was injected. Symbols: circles, animals with adrenal medullary transplants in the spinal cord (n=12); squares, animals with control transplants in the spinal cord. Comparisons between the two groups using two-way ANOVA indicated that the induction of analgesia was statistically significant for all three tests ($P<0.01$, tail flick and hot plate tests; $P>0.05$, paw pinch test);

FIG. 6 shows the effect of nalonone on the analgesia induced by spinal cord adrenal medullary transplants. The ordinate is the threshold for response to noxious stimuli as assessed by the tail flick test (A), hot plate test (B), or paw pinch test (C). Each point represents the mean ±S.E.M. The abscissa is the time course of responses to noxious stimuli following drug injections. Time 0 indicates the pre-injection values. The closed arrowhead indicates the point at which nicotine (0.1 mg/kg, s.c.) was injected. Following the induction of analgesia, animals received either naloxone (2 mg/kg, s.c.) or saline vehicle, indicated at the open arrowhead. Symbols: circles, animals with spinal cord adrenal medullary transplants receiving naloxone following the induction of analgesia (n=9); squares animals with spinal cord adrenal medullary transplants receiving saline following the induction of analgesia (n=9). Comparisons between the two groups using two-way ANOVA indicated that the reversal of the analgesia by naloxone was statistically significant for all three tests ($P<0.01$)

DETAILED DESCRIPTION OF INVENTION

The above and other objects and advantages of the present invention are achieved by a novel method of relieving pain comprising implanting in the CNS of a host susceptible to pain, living cells or tissues capable of releasing effective amount of analgesic substances when interacted with a stimulus which induces said cells or tissues to release analgesic substances including opioid peptides and catecholamines. Of course, any suitable type of living material can be employed so long as such material is transplantable in the CNS without rejection and has the inherent property of locally or systemically releasing in the tissue, body or body fluid analgesic substances under appropriate conditions. Preferred examples of such material are isolated, substantially homogeneously purified bovine chromaffin cells and adrenal medullary tissues. Implantation of such material can be done at any suitable site in the CNS where nociceptors are accessibly present. Typical examples of such sites are spinal cord, and the brainstem, particularly the dorsal horn, the subarachnoid space of the lumbar region, substantia gelatinosa, the periaqueductal gray, the nucleus raphe magnus, the nucleus reticularis gigantocellularis and the like. Implantation in one or more of such regions would provide a permanent and continuous local source of neuroactive substances, thus providing a means for permanent relief of pain or for reducing sensitivity to intractable pain. Moreover, the level of pain relief can be easily controlled or modulated pharamacologically by using any agent which stimulates receptors on the implanted cells, such as nicotine or muscarinic agonists and the like. Analgesia thus induced can also be conveniently manipulated or reversed by such antagonists as the opiate antagonist naloxone, adrenergic antagonist phentolamine, ganglionic antagonist mecamylamine, and the like. Stimulation or modulation of implanted cells can, of course, also be achieved by other means such as delivering pulses of electrical current through micro-electrodes and the like.

Unless specifically defined otherwise, all scientific or technical terms used herein have the same meaning as generally understood in the art to which the present invention belongs and all publications mentioned hereunder are incorporated herein by reference. Although any similar or equivalent methods and materials can be conveniently adopted in the practice or testing of the invention disclosed herein, the preferred methods and mateials are now described.

MATERIALS AND METHODS

In all of the following studies, male Sprague-Dawley derived rats weighing 300–500 grams served as hosts. Pain sensitivity was measured in these animals using three standard analgesiometric tests sequentially: the tail flick test, the paw pinch test, and the hot plate test.

To elicit the tail flick response, a focused beam of high intensity light is applied to the dorsal surface of the rat's tail. The time interval between the onset of the stimulus and the tail flick response is measured at three regions of the tail, the average of which is defined as the "tail flick latency". To prevent tissue damage in the absence of a response, the stimulus is terminated at 14 seconds and the tail flick latency is assigned a value of 14. The paw pinch response is elicited by a commercially available apparatus (Ugo-Basile) which applies pressure at a constant rate of 64 grams/sec. The force is applied to the ventral surface of both hind paws sequentially until the animal reacts by a withdrawal response. The hot plate response is determined by placing the rat on a 55° C. copper plate enclosed in a plexiglass cylinder. The interval between placement on the hot plate is defined as the "hot plate latency". In the absence of a response, the animal is removed after 40 seconds and assigned a hot plate latency of 40. Thus, both thermal and mechanical pain stimuli were employed, as well as both reflexive and integrated pain response were monitored. In all of the following studies, animals were initially screened for baseline pain sensitivities and pain sensitivities following a low dose of nicotine (0.1 mg/kg, subcutaneously).

EXAMPLE 1

The isolated chromaffin cells were obtained from the adrenal glands of steers or cows as described by Pollard et al., J. Biol. Chem. 259:1114–1121 (1984). The resultant preparation from 7-9 glands contains about $0.5–1.0 \times 10^9$ chromaffin cells and is substantially pure, that is essentially free of other cell types. Suspensions of primary cultures of bovine chromaffin cells were obtained in air-tight culture media at 4° C. the day after preparation. Of course, it should be understood that bovine source for chromaffin cells is used simply because of convenience and easy availability. But, any other source which is deemed suitable can be equally well used, the source per se of the tissue or cells not being a critical feature of the invention.

For implantation, the cells were concentrated by centrifugation and resuspended in small volumes of Hank's buffer containing 0.1 µg/ml 2.5 S nerve growth factor and kept on ice until they were placed in the rat spinal cords. The cells were injected via an intrathecal catheter according to a modification of the technique of Yaksh and Rudy, Physiol. Behav. 27:1031–1036(1976). Under ether anesthesia, a small incision was made in the dura overlying the atlanto-occipital junction, a catheter made of polyethylene (PE 10) tubing was threaded through the incision into the subarachnoid space and down the spinal cord to the level of the lumbar enlargement. Cell suspensions were injected through the catheter in 15 µl volumes over 20–30 seconds, followed by a 10 µl flush with Hank's buffer. Each animal received approximately 100,000 cells (counted in a hemocytometer). Cell viability was determined at the end of the surgical procedures by trypan blue exclusion to be 80–90%. Control animals received equal volumes of either heat-skilled cells or only Hank's buffer containing nerve growth factor.

Animals which exhibited motor abnormalities following surgical procedures were discarded from the study. The remaining animals were returned to their cages and allowed free access to food and water. They were tested for pain sensitivities according to the protocols described hereunder.

Test 1

Initially, animals were tested 6–8 weeks following cell implantation, since this was determined to be sufficient for establishment of behavioral responses. Pain sensitivity was assessed for implanted and control animals by the three analgesiometric tests listed above. The animals then received an injection of nicotine (0.1 mg/kg, s.c.), and were tested again 2, 10, 20, and 30 minutes later.

Test 2

In order to determine the potential for long term changes in pain sensitivity, another group of animals with identical implants were tested for pain responsiveness before and after nicotine at several time intervals following the implantation procedures. Rats were tested at 1 day, 1 week, 2 weeks, 4 weeks, 8 weeks, and 16 weeks after receiving cell or control implants.

Test 3

To determine the sensitivity of chromaffin cell implants to nicotine, another group of implanted animals received several doses of nicotine at weekly intervals on a rotating dose schedule. The doses of nicotine used were 0.05 mg/kg, 0.1 mg/kg, and 0.2 mg/kg.

Test 4

Since the analgesia induced by stimulation of chromaffin cells may be due to the release of neuroactive substances from chromaffin cell granules, it was important to determine the contribution of catecholamines and opioid peptides to this response. Rats with spinal cord bovine chromaffin cell implants received an injection of either opiate antagonist naloxone (2 mg/kg, s.c.), alpha-adrenergic antagonist phentolamine (10 mg/kg, s.c.), or saline vehicle 5 minutes before the nicotine injection. These antagonist doses were chosen since they do not produce any alterations in pain sensitivity (Jensen et al., Eur. J. Pharmacol. 86:65–70, 1983).

Statistical analysis was done using two-way analysis of variance (ANOVA) and the Newman-Keuls test for multiple post-hoc comparisons (Keppel et al., Design and Analysis: A Researcher's Handbook, 1973).

Figure 1A:
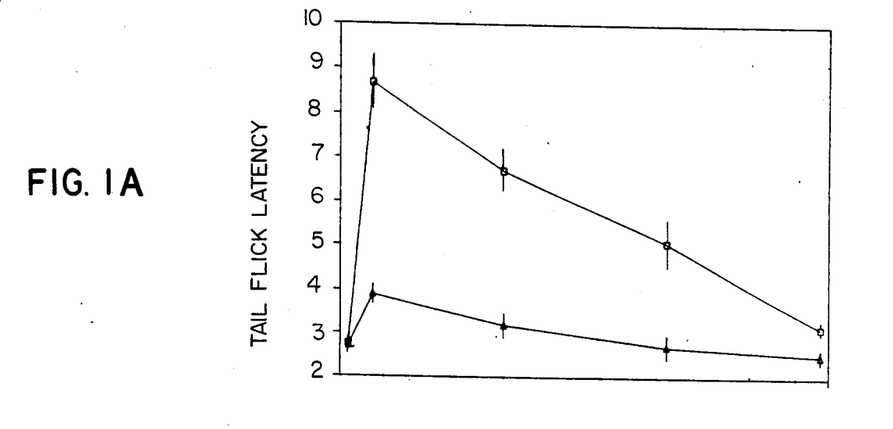
FIG. 1 shows the effect of spinal cord bovine chromaffin cell implants on pain sensitivity. The ordinate is the threshold for response to noxious stimuli as measured by the: (A) tail flick test (sec), (B) paw pinch test, and (C) hot plate test (sec). Each point represents the mean +/−S.E.M. The abscissa is the time course of responses (min) to noxious stimuli following nicotine stimulation. Time 0 indicates the pre-injection values. The arrowhead indicates the point at which nicotine (0.1 mg/kg, s.c.) was injected. Symbols: squares, animals with bovine chromaffin cell implants in the spinal cord (n=14); triangles, animals with control implants in the spinal cord (n=10)
Figure 1B:
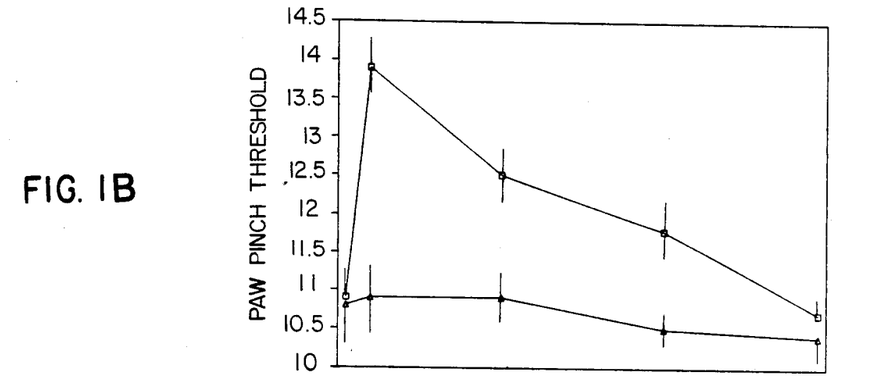
Figure 1C:
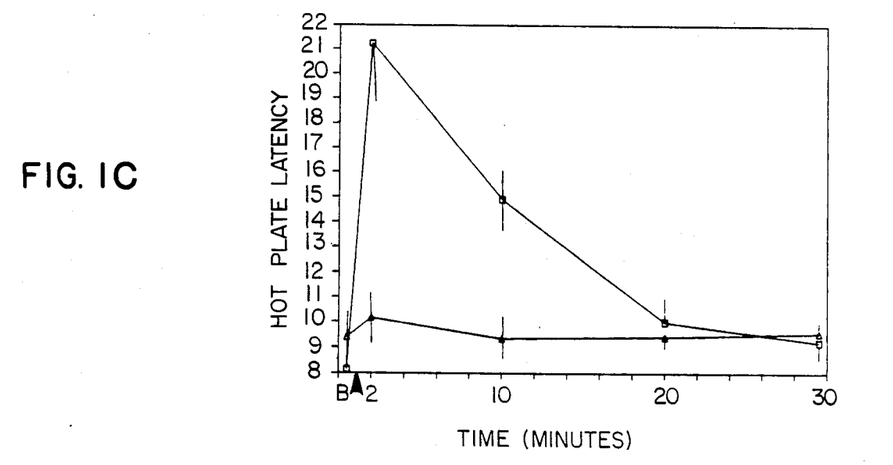

The results indicated that prior to the implantation of chromaffin cells, nicotine (0.1 mg/kg) did not produce any alterations in pain sensitivity as assessed by the tail flick, paw pinch, or hot plate tests. In contrast, the injection of nicotine induced potent analgesia in animals with spinal cord chromaffin cell implants ($P<0.01$ for all three tests). The results are shown in FIG. 1. The peak increase in pain threshold was at 2 minutes following the nicotine injection. Both tail flick latency and paw pinch threshold remained elevated for 20 minutes, tending toward baseline levels by 30 minutes, while hot plate latencies returned to baselines by 20 minutes. The injection of nicotine had not significant effect on pain sensitivity in animals with control implants.

Figure 3A:
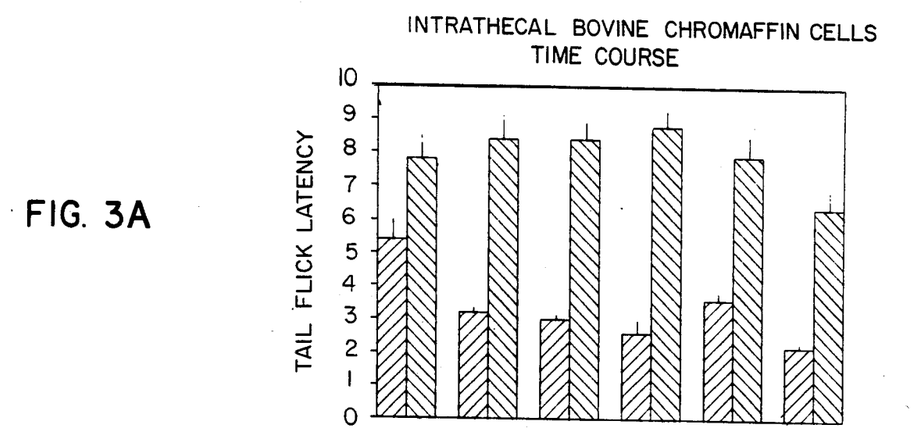
FIG. 3 shows long-term changes in pain responsiveness in animals with spinal cord bovine chromaffin cell implants. The ordinate is the threshold for response to noxious stimuli as determined by: (A) the tail flick test (sec), (B) the paw pinch test, and (C) the hot plate test (sec). The bars represent the mean +/−S.E.M. for each measurement (n=15 animals). The ordinate is the time (days) after chromaffin cell implantation. Each set of bars represents the response latencies before and 2 minutes after nicotine injections (0.1 mg/kg, s.c.) in implanted animals. Since nicotine had no effect on pain sensitivity in animals with control implants at any of these times, these values are omitted for clarity.
Figure 3B:
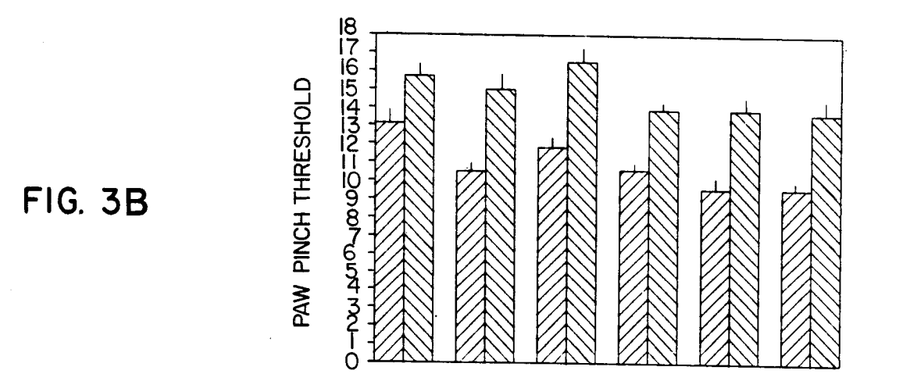
Figure 3C:
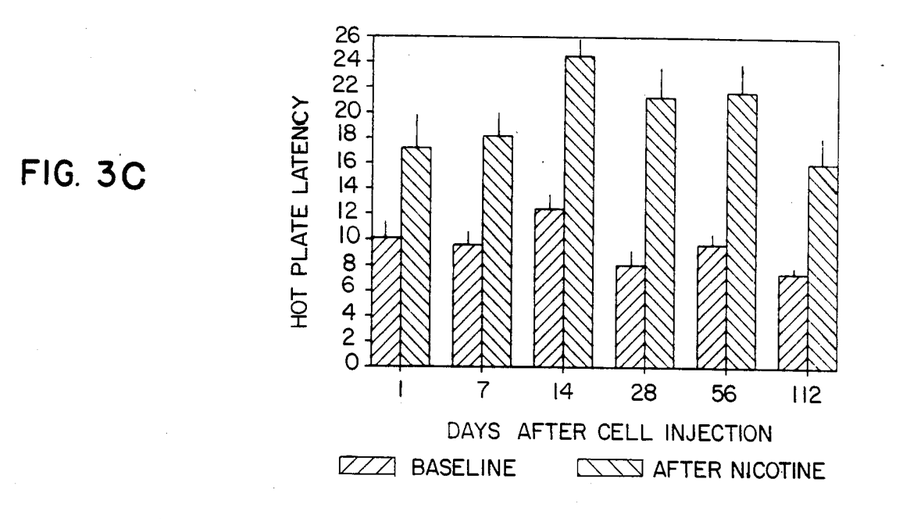

The ability of nicotine to induce analgesia in implanted animals was tested at several intervals over a 16 week period. Results are summarized in FIG. 3. Since this dose of nicotine did not significantly alter pain sensitivity at any time in control animals ($P>0.05$), the data for these animals has not been included herein. Analgesia induced by nicotine stimulation could be observed as early as one day following cell implantation. However, at this time, the difference between the pre- and post-nicotine response latencies were smaller than at other time points, particularly for the tail flick and paw pinch tests. An explanation for this is that the baseline pain sensitivities (pre-nicotine) were higher at one day following cell implantation than at other times during the study. Compared to the pre-implantation pain sensitivities, tail flick latency was elevated from $3.2+/-0.4$ sec to $5.4+/-0.06$ sec and paw pinch threshold from $10.5+/-0.5$ to $13.1+/-0.7$. These differences were statistically significant ($P<05$).

The ability to induce analgesia with nicotine in transplanted animals was well maintained for at least up to 4 months. The differences between the pre- and post-nicotine pain sensitivities were statistically significant at all the tested time points for all three tests ($P<0.01$). However, there appeared to be a slight decrement in response toward the end of the study, although this was not statistically significant.

Figure 4A:
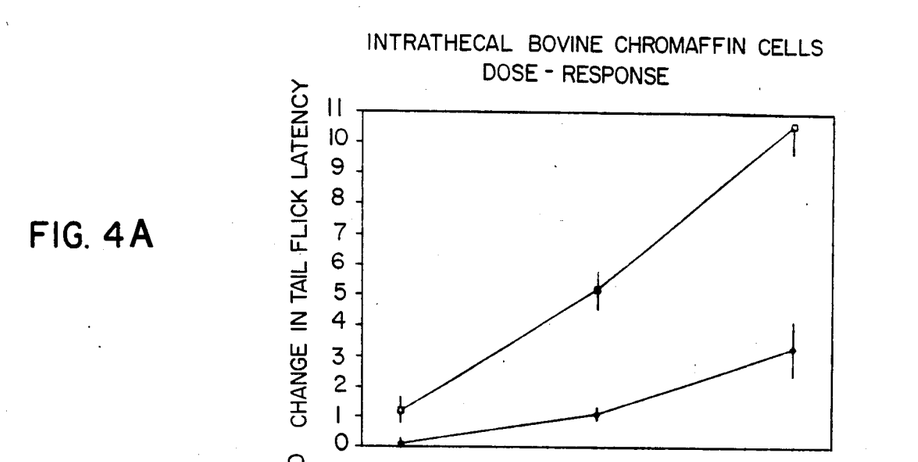
FIG. 4 shows dose-response relationships for the effect of nicotine on pain sensitivity in animals with spinal cord bovine chromaffin cell implants. Ordinate: Changes in nociceptive threshold for: (A) tail flick test (sec), (B) paw pinch test, and (C) hot plate test (sec). Values were obtained by subtracting the pre-nicotine response latencies from the latencies determined 2 minutes following nicotine injections. Each point represents the mean +/−S.E.M. Abscissa: nocotine doses (mg/kg) plotted on a log scale. Symbols: Squares, animals with bovine chromaffin cell implants in the spinal cord (n=9); diamonds, animals with control implants in the spinal cord (n=8)
Figure 4B:
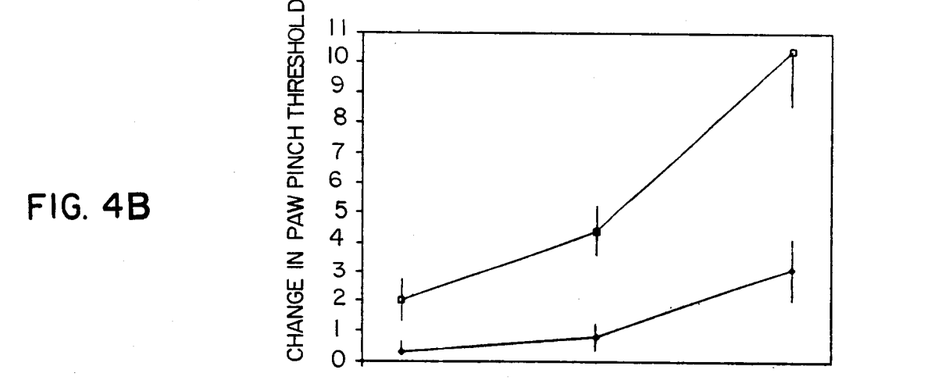
Figure 4C:
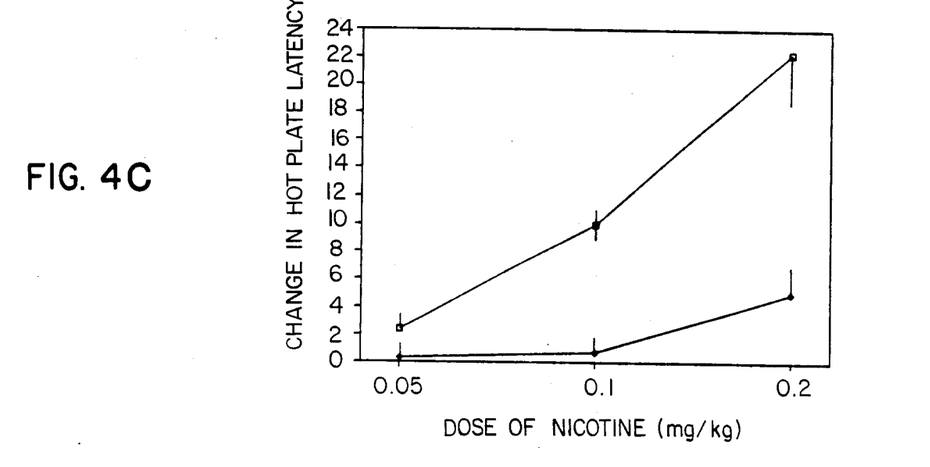

The sensitivity of the implanted chromaffin cells to low doses of nicotine was determined by using several doses of nicotine. Results are illustrated in FIG. 4. The lowest dose of nicotine, 0.05 mg/kg, produced a small, but statistically significant elevation in tail flick latency in animals with spinal cord bovine chromaffin cell implants ($P<0.05$). This dose also appeared to produce an increase in paw pinch threshold and hot plate latency, but these were not statistically significant. At the highest dose of nicotine (0.2 mg/kg), the elevations in all three tests were nearly maximal (91% maximum tail flick latency, and 92% maximum paw pinch threshold). However, at this dose, there was also a small but significant elevation in the pain threshold of control animals.

Figure 5A:
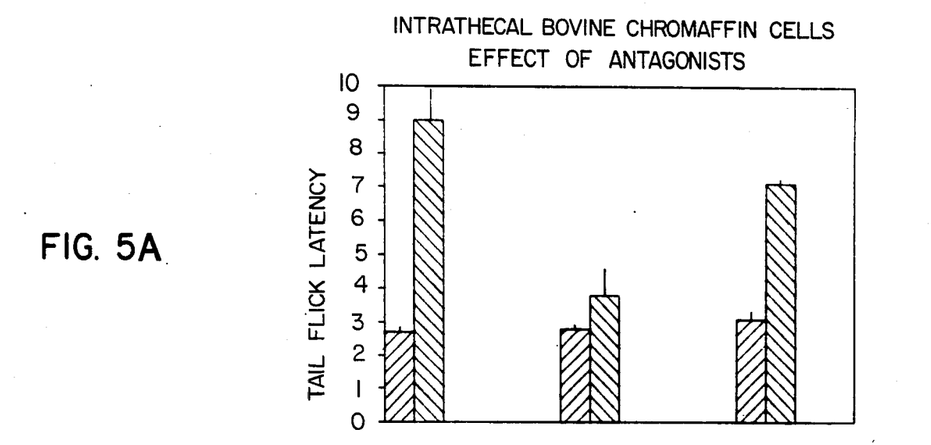
FIG. 5 shows the effect of antagonists on the analgesia induced by nicotine in animals with spinal cord bovine chromaffin cell implants. The ordinate is the threshold for response to noxious stimuli as determined by: (A) the tail flick test (sec), (B) the paw pinch test, and (C) the hot plate test (sec). Each bar represents the mean +/−S.E.M. (n=7). The first bar in each set is the pain threshold measured 5 minutes following the injection of either saline, naloxone (2 mg/kg, s.c.), or phentolamine (10 mg/kg, s.c.). The pre-injection values are not shown, since the antgonists did not alter these response latencies. The second bar in each set is the response to nicotine (0.1 mg/kg, s.c.), injected 5 minutes after the pretreatment with antagonists.
Figure 5B:
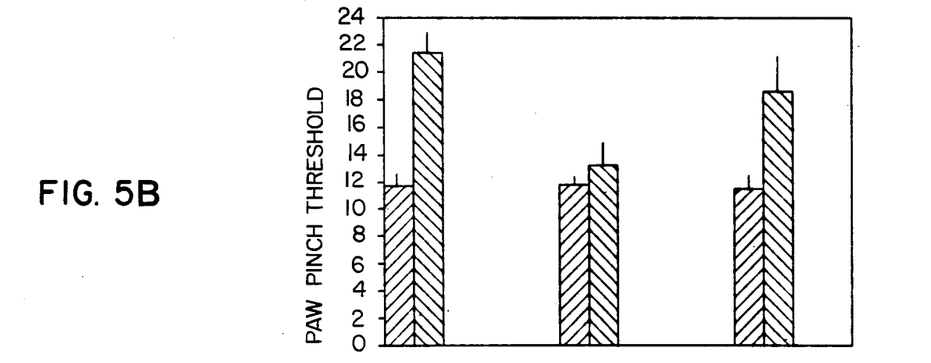
Figure 5C:
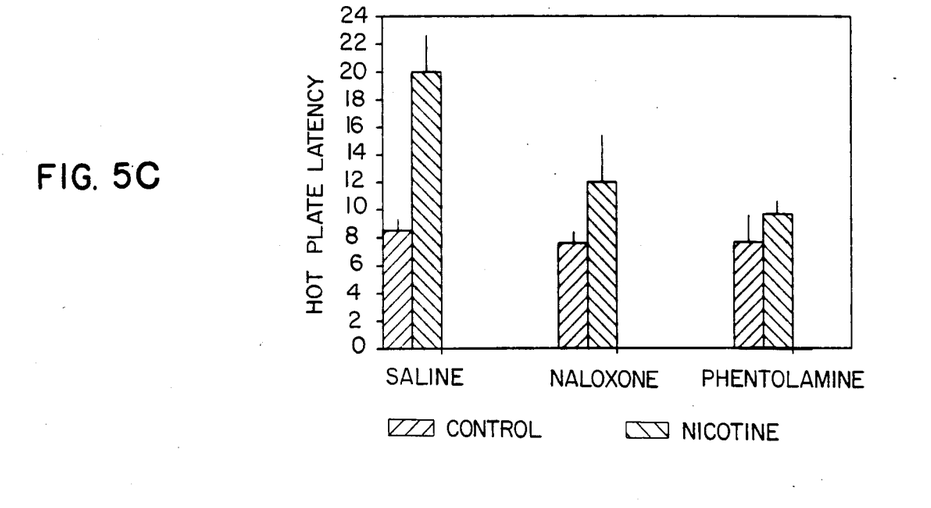

In order to determine the contribution of catecholamines and opioid peptides to the analgesia induced by nicotine in implanted animals, a group of animals with spinal cord bovine chromaffin cell implants was pretreated with either opiate antagonist naloxone, adrenergic antagonist phentolamine, or saline vehicle. These pre-injections did not alter pain sensitivity as determined 5 minutes after the injection (not shown). The injection of nicotine (0.1 mg/kg) in saline pretreated animals resulted in the usual induction of analgesia (FIG. 5). In contrast, this analgesia was severely attenuated in animals pretreated with naloxone as assessed by all three analgesiometric tests (P<0.01). Phentolamine pretreatment completely blocked the elevation in hot plate latency (P<0.01), and appeared to partially attenuate the elevation in tail flick latency and paw pinch threshold, but these were not statistically significant.

EXAMPLE 2

Adrenal tissue for transplantion was obtained from female Sprague-Dawley derived rats of the same group as the host animals. Adrenal medullary tissue was dissected from cortical tissue, cut into small pieces (less than 0.5 cu. mm.), and incubated in 2.5 S nerve growth factor (0.1 g/ml) in Hank's buffer containing 1 mg/kg bovine serum albumin) for 20 minutes. Tissue from one adrenal medulla was transplanted in each animal. Control animals received an equal volume of either heat killed adrenal medullary tissue or sciatic nerve tissue. Under pentobarbital anesthesia (30 mg/kg, i.p.), a laminectomy was performed to expose a 2–3 mm segment of the lumbar enlargement. Under a dissecting microscope, a small incision was made in the dura and pieces of adrenal medulla were placed in the subarachnoid space and pushed under the dura to keep them in place. The skin was closed with wound clips and the animals returned to their cages for observation. Animals exhibiting motor abnormalities following surgical procedures were discarded from the study.

Figure 2A:
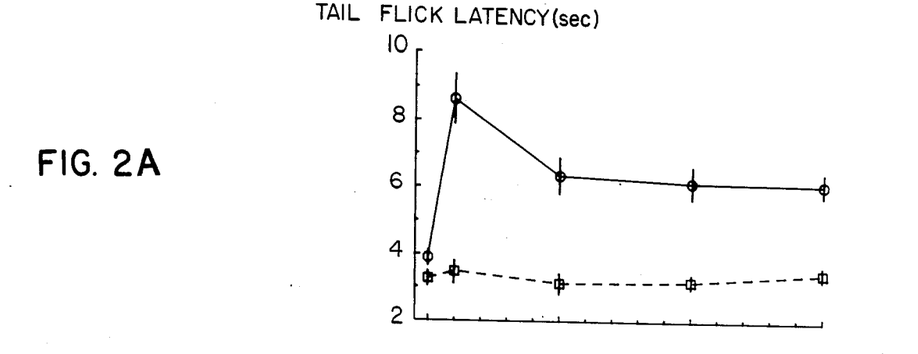
Figure 2B:
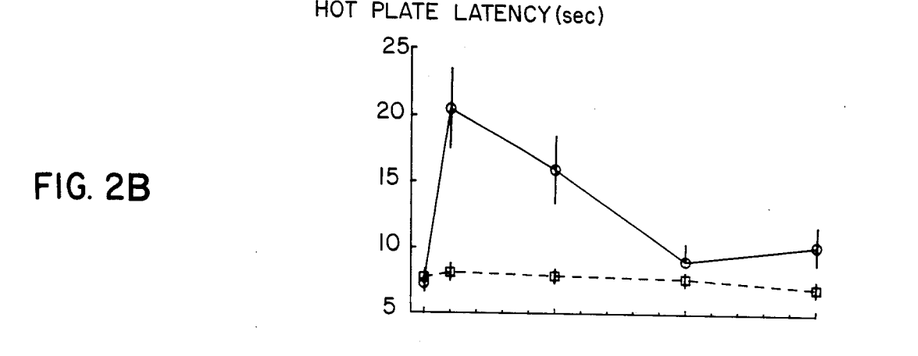
Figure 2C:
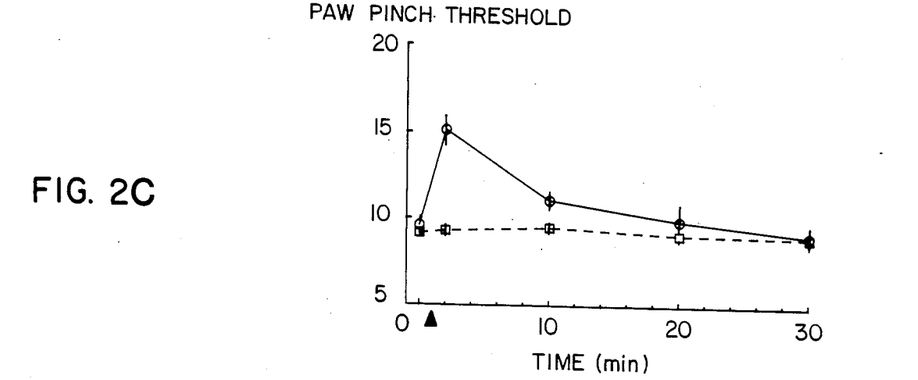
Figure 6A:
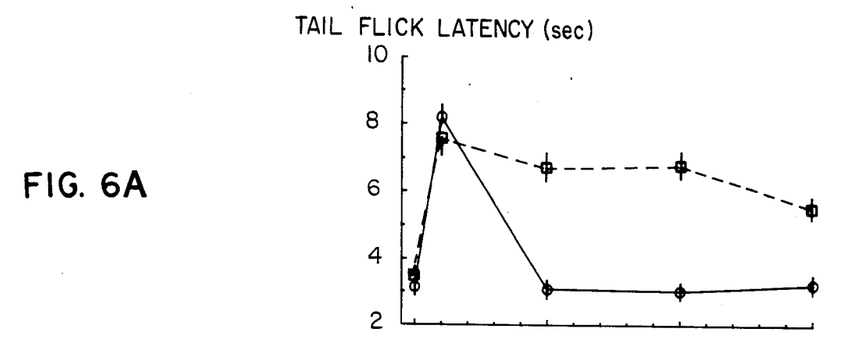
Figure 6B:
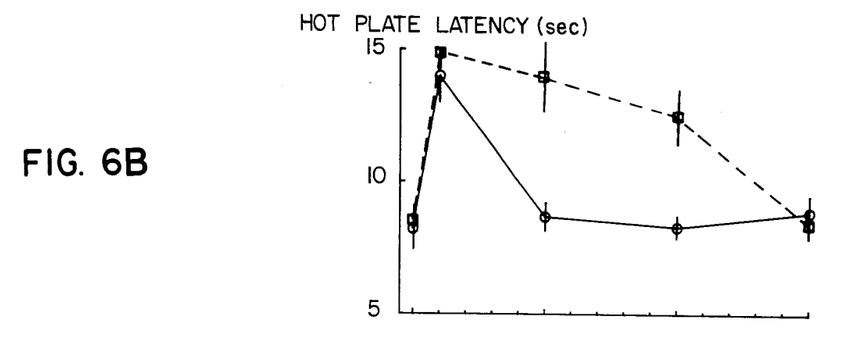
Figure 6C:
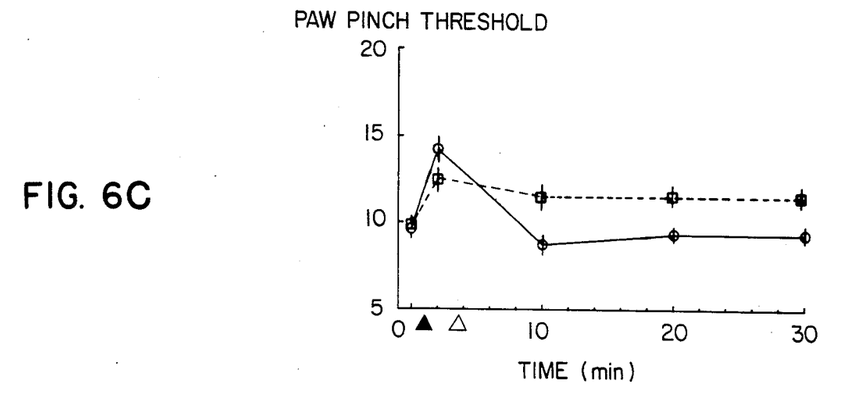

Pain sensitivity was determined at several intervals following transplantation, but the 8 week time point is used here since morphological studies have shown that the grafts are well established by this time. Following determination of pain sensitivity in transplanted animals, response to nicotine stimulation (0.1 mg/kg, s.c.) was measured at 2, 10, 20, and 30 minutes following the injection. Results of this study are shown in FIG. 2. Animals receiving control transplants of either killed adrenal tissue or sciatic nerve tissue were pooled since there was no difference in their responses. Pain sensitivity in pre-implanted animals (not shown) was 3.2±0.2 sec., 7.7±0.8 sec., and 9.5±0.5, for the tail flick, hot plate, and paw pinch tests, respectively. The injection of nicotine had no effect on the pain threshold of these animals prior to implantation. Similarly, the injection of nicotine did not alter pain responsiveness in control transplant animals (FIG. 2). In contrast, this dose of nicotine produced potent analgesia in animals with spinal cord adrenal medullary transplants. The reduction in pain responsiveness was observed for all three analgesiometric tests (FIG. 2). This analgesia was apparent 2 minutes following nicotine stimulation, and pain threshold remained elevated for 10–20 minutes following the injection, tending toward baseline by 30 minutes. FIG. 6 shows the effect of antagonists (naloxone and phentolamine) on adrenal medulla transplanted animals. The results are similar to those observed with chromaffin cell implanted animals.

Figure 7:
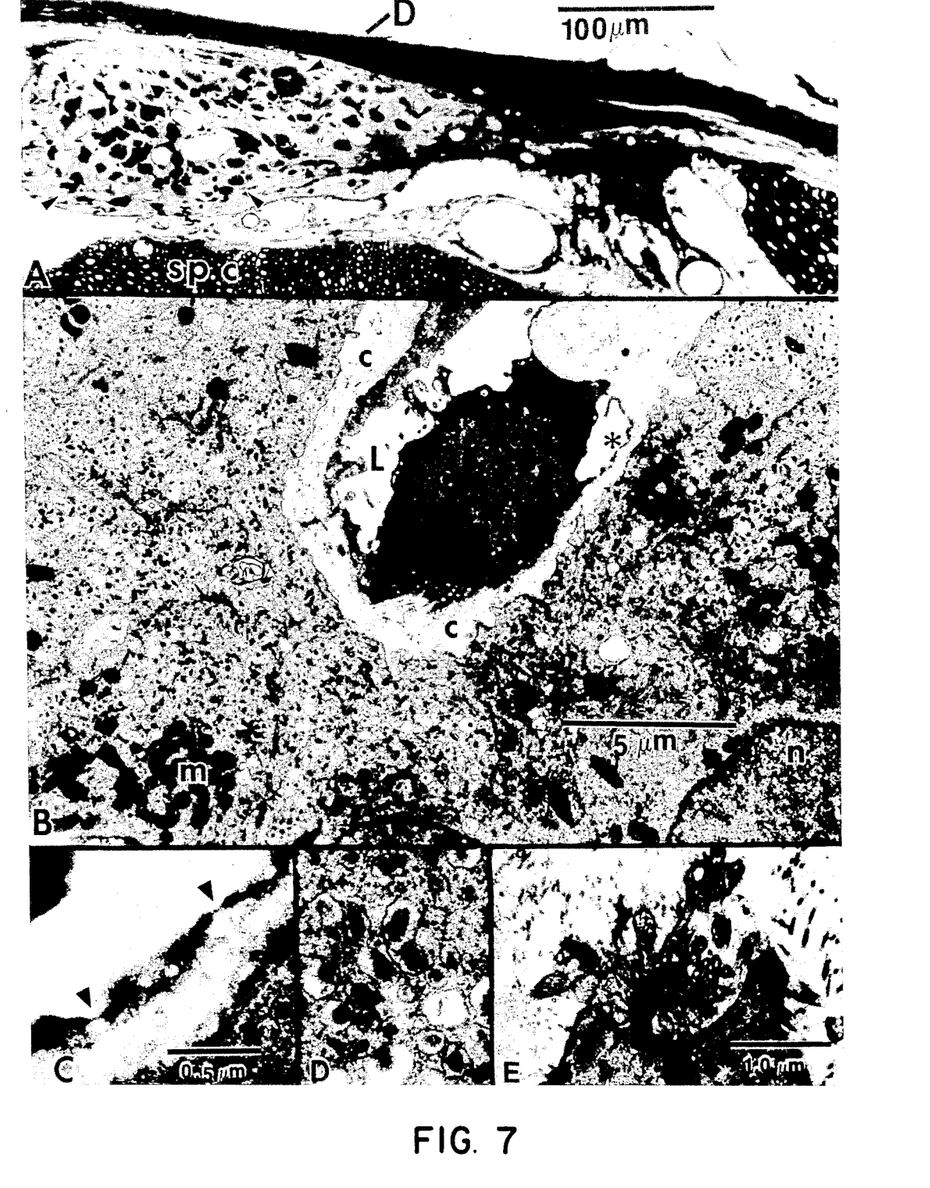
FIG. 7A shows light micrograph of a section from a portion of the dorsal lumbar spinal cord. A piece of adrenal medullary transplant can be found in the subdural space. Dense chromaffin cells can be readily identified in the graft (arrowheads). D=dura; spc=spinal cord.
FIG. 7B shows the electron micrograph of adrenal medullary tissue that was transplanted for eight weeks in the spinal cord. The graft is made up primarily of compact granulated chromaffin cells (See enlargement of chromaffin granules at asterisk in D). Note that portions of the blood vessel endothelial cells are attenuated and fenestrated. (See C. which is an enlargement of the endothelial process at the asterisk)
FIG. 7C shows the diaphragms at arrowheads in the fenestrae of the endothelial process.
FIG. 7D shows that the granules are of the norepinephrine type, in contrast to the predominant epinephrine type found in the rat adrenal medulla in situ.
FIG. 7E shows the enlarged portion of a chromaffin cell in the subarachnoid space of the dorsal spinal cord where some short blunt processes are present eight weeks following transplantation.

In order to determine the underlying morphological changes responsible for the observed alterations in pain sensitivity, animals were prepared for electron microscopy following termination of behavioral testing. Animals were deeply anesthetized and perfused via the aorta with saline followed by buffered mixed aldehydes. The spinal cords were removed and processed for electron microscopy following standard procedure. The transplanted tissue was readily identified under a dissecting microscope and toluidine blue stained semi-thin sections revealed that the transplants were healthy and contained numerous chromaffin cells (FIG. 7A and 7B). Ultrastructural observations revealed that the chromaffin cells in the transplants contained many chromaffin granules, primarily of the nonrepinephrine containing type (FIG. 7B and 7D). The capillaries in the transplants appear to be fenestrated (FIG. 7C), in contrast to those of the host central nervous system, providing a potential for leakiness in the blood-brain barrier. It is noted that there did not appear to be extensive interaction between the graft tissue and the host centrall nervous system, although finger-like projections containing chromaffin granules can occasionally be seen protruding from chromaffin cells in the graft (FIG. 7E). Thus it does not appear that synaptic relationships between the host and graft tissue are a necessary prerequisite for behavioral alterations. Rather, it is likely that the observed alterations in pain sensitivity are due to the humoral release of pharmacologically active substances into the subarachnoid space or cerebrospinal fluid in the CNS.

The data presented herein clearly demonstrates that pain sensitivity, particularly to intractable pain as evidenced by hot-plate test, is alterable by implanting adrenal medullary tissue or isolated chromaffin cells into the subarachnoid space of the spinal cord. The ability of low dose of nicotine to induce analgesia in implanted animals suggests that the implanted material survives and retains functional ability to respond to nicotinic stimulation by releasing pain altering substances. Since this transplant is cross-species (bovine cells into rat CNS), it again emphasizes the immunological privilege of the CNS. Classical studies have suggested that the CNS is immunologically protected, and tissues with major histocompatibility differences transplanted to the CNS are rarely completely rejected. In support of this, Perlow et al., supra, have shown that dispersed, cultured bovine chromaffin cells survive at least 2 months without evidence of immunological rejection when transplanted to the cerebral ventricles of rats. In addition, these transplanted cells maintain the ability of synthesize and store catecholamines, as indicated by fluorescence histochemistry (not shown).

These results further indicate that analgesia can be induced as early as one day following transplantation. The changes brought about by the implants appear to be maintained for at least 4 months since nicotine could still induce analgesia at this time. This suggests that neural tissue transplanted across species may provide a long-term therapeutic approach to treating intractable pain.

The response to nicotine stimulation is dose-related, suggesting that the implants respond to higher doses with an increased release of nicoceptor interacting substances. At the highest dose of nicotine, the increase in pain threshold was nearly maximal for the tests employed. However, the intermediate dose of 0.1 mg/kg was determined to be optimal for these studies, since this dose by itself does not alter pain sensitivity in these animals.

The ability of naloxone to block the analgesia normally induced by nicotine in the implanted animals supports the notion that this analgesia is the result of the release of opioid peptides from the transplanted chromaffin cells. The partial attenuation by phentolamine suggests that catecholamine release may also be involved. It is possible that other neuropeptides in the chromaffin cells may also be involved. Thus, the co-release of two or more pharmacologically active agents, such as norepinephrine and enkephalin, from implanted chromaffin cells would act synergistically to produce paian relief. Whatever the mechanism, the results clearly demonstrate the efficacy of the methods described herein for relieving and/or modulating sensitivity to pain. The technique disclosed herein provides a new therapeutic approach for the relief of intractable pain.

It is understood that the examples and embodiments described herein are for illustrative purposes only and that various modifications or changes in light thereof will be suggested to persons skilled in the art and are to be included within the spirit and purview of this application and the scope of the appended claims.

We claim:

1. A method of inducing analgesia or reducing pain comprising implanting isolated, substantially homogeneously purified chromaffin cells or adrenal medullary tissue in nociceptor region of central nervous system of a host susceptible to pain, and stimulating said cells or tissue by infecting a nicotinic or muscarinic agonist to release effective amount of analgesic substance to reduce pain.

2. The method of claim 1 wherein said material is isolated, substantially homogeneously purified bovine chromaffin cells.

3. The method of claim 2, wherein said nociceptor region is in spinal cord or brain stem.

4. The method of claim 1 wherein said stimulus is nicotine.

5. The method according to claim 1, of reversing the release of analgesic substance by an antagonist.

6. The method of claim 5 wherein said antagonist is selected from the group consisting of opiate antagonist, adrenergic antagonist and ganglionic antagonist.

7. The method of claim 6 wherein said antagonist is naloxone.

8. The method of claim 3, wherein the nociceptor region in the spinal cord is dorsal horn of lumbar region.

9. The method of claim 8, wherein the nociceptor region in the spinal cord is subarachnoid space of dorsal horn of lumbar region.

10. The method of claim 3, wherein the nociceptor region in the spinal cord is substantia gelatinosa.

11. The method of claim 3, wherein the nociceptor region in the brain stem is selected from the group consisting of peraqueductal gray, nucleous raphe magnus and nucleus reticularis gigantocellularis.

12. The method of claim 11, wherein the nociceptor region is periaqueductal gray.

13. The method of claim 11, wherein the nociceptor region is nucleus raphe magnus.

14. The method of claim 11, wherein the nociceptor region is nucleus reticularis giganticellularis.

* * * * *